(12) United States Patent
Schulz et al.

(10) Patent No.: US 7,115,773 B2
(45) Date of Patent: Oct. 3, 2006

(54) COUPLED PRODUCTION OF TWO ESTERS

(75) Inventors: Eckhard Schulz, Bad Homburg (DE); Helmut Bauer, Frankfurt (DE); Klaus Dieter Merscher, Buttelborn (DE)

(73) Assignee: Celanese Chemicals Europe GmbH, (DE)

( * ) Notice: Subject to any disclaimer, the term of this patent is extended or adjusted under 35 U.S.C. 154(b) by 0 days.

(21) Appl. No.: 10/380,870

(22) PCT Filed: Sep. 7, 2001

(86) PCT No.: PCT/EP01/10349

§ 371 (c)(1),
(2), (4) Date: Mar. 14, 2003

(87) PCT Pub. No.: WO02/22547

PCT Pub. Date: Mar. 21, 2002

(65) Prior Publication Data

US 2003/0176728 A1   Sep. 18, 2003

(30) Foreign Application Priority Data

Sep. 16, 2000  (DE) ............................... 100 45 894

(51) Int. Cl.
*C07C 67/48* (2006.01)
(52) U.S. Cl. .................................................... 560/248
(58) Field of Classification Search ................ 560/129, 560/179, 231, 265
See application file for complete search history.

(56) References Cited

U.S. PATENT DOCUMENTS 6,093,845 A * 7/2000 van Acker et al. .......... 560/239

FOREIGN PATENT DOCUMENTS

| GB | 1394651 | 5/1975 |
| WO | 98/45652 | * 10/1998 |
| WO | 9842652 | 10/1998 |

OTHER PUBLICATIONS

Kirk-Othmer Encyclopedia of Chemical Technology Copyright © 1994 by John Wiley & Sons, Inc. Article Online Posting Date: Dec. 4, 2000.*

* cited by examiner

*Primary Examiner*—Thurman K. Page
*Assistant Examiner*—Karl Puttlitz
(74) *Attorney, Agent, or Firm*—Charles A. Muserlian

(57) ABSTRACT

The invention relates to a method for the coupled production of two esters by reacting a mixture of aliphatic alcohols with an aliphatic carboxylic acid and then treating the resulting mixture by distillation. During the distillation process, a side flow that is taken from the distillation column that is connected downstream of the esterification reactor is fed back into said esterification reactor. The pure ester compounds are obtained from the bottom of the distillation columns that are connected downstream of the esterification reactor.

11 Claims, 1 Drawing Sheet

COUPLED PRODUCTION OF TWO ESTERS

This application is a 371 of PCT/EP01/10349 filed Sep. 7, 2001.

The invention relates to the coupled production of two esters by reacting a mixture of aliphatic alcohols with an aliphatic carboxylic acid and then working up the mixture by distillation to give the pure ester compounds.

Esters of aliphatic alcohols and carboxylic acids are of considerable industrial importance as solvents. Thus, for example, ethyl acetate and n-butyl acetate are widely used as solvents in the paint and finish industry. Esters of aliphatic alcohols and aliphatic carboxylic acids are also used in the production of cellophane, celluloid, collodium wool and synthetic resins. Acrylates, such as, for example, butyl acrylate or 2-ethylhexyl acrylate are preferably used in the coatings and adhesives sector and in the conversion of paper and finishing of textiles and leather. Furthermore, acrylates are important monomers for the preparation of polyacrylates.

The direct esterification of alcohols with carboxylic acids is one of the fundamental operations of organic chemistry. In order to steer the reaction in the direction of the desired ester, it is expedient to remove the water of reaction continuously. Suitable measures are, for example, azeotropic distillation, heating the reaction mixture with passage of an inert gas, carrying out the reaction in vacuo or the presence of a drying agent. The azeotropic distillation can be carried out in the presence of an added water-immiscible entraining agent. However, it is also possible for acid or alcohol present in excess to serve as an entraining agent. The component which has the lower boiling point is expediently chosen to be present in excess.

The reaction can be carried out in the absence of catalysts but then requires higher temperatures and longer reaction times. Both reaction conditions can be made milder with the use of acidic catalysts. In addition to sulfuric acid, organic acids, such as methanesulfonic acid, p-toluenesulfonic acid and cation exchangers of the polystyrene sulfonic acid type, are the preferred catalysts.

Residual alcohol contents which may not exceed specific limits of many applications constitute an important quality criterion for desired ester reaction volume and distillation volume. The coupled production therefore leads to savings in the capital costs and in the steam consumption.

In spite of the advantages described, the distillation process to be carried out according to the proposal of GB-1,394,651 leads to a butyl acetate having considerable residual contents of n-butanol, since the residual amounts of n-butanol leaving the esterification column via the top all enter the pure butyl acetate fraction. For many applications, however, it is necessary to provide a butyl acetate having as low a residual n-butanol content as possible.

A further process for the coupled production of ethyl acetate and butyl acetate is disclosed in WO 98/42652. There, after the volatile fractions have been separated off, the crude esterification mixture is added to a separation column and is separated into ethyl acetate as top product and butyl acetate as bottom product. A liquid side stream which contains impurities, for example, butanol or crotonaldehyde, is taken off from the separation column and is discarded. According to the teaching of WO 98/42652, impurities which contain the carboxyl group can be removed by treatment with a polymeric resin, it being possible for the starting compounds or the finished ester products to be treated with a polymeric resin which is loaded, for example, with bisulfite ions in order to fix aldehyde impurities.

It was therefore the object to provide a process for the coupled production of two esters, in which two ester compounds are obtained in excellent purity and with low residual contents of starting alcohols.

This object is achieved by a process for the coupled production of two esters by reacting a mixture of two aliphatic alcohols with an aliphatic carboxylic acid and working up the crude ester mixture by distillation. In the process, after the water of reaction has been separated off, the crude ester mixture leaving the esterification reactor is fed to a first distillation column, in which a side stream containing the higher-boiling alcohol component is taken off below the feed point of the crude ester and is recycled to the esterification reactor, in which the higher-boiling ester compound is taken off via the bottom and in which, after water has been separated off, the top take-off is fed to a second distillation column, in which the low-boiling ester compound is taken off via the bottom and in which, after water has been separated off, the top take-off is recycled to the esterification reactor.

Figure 1:
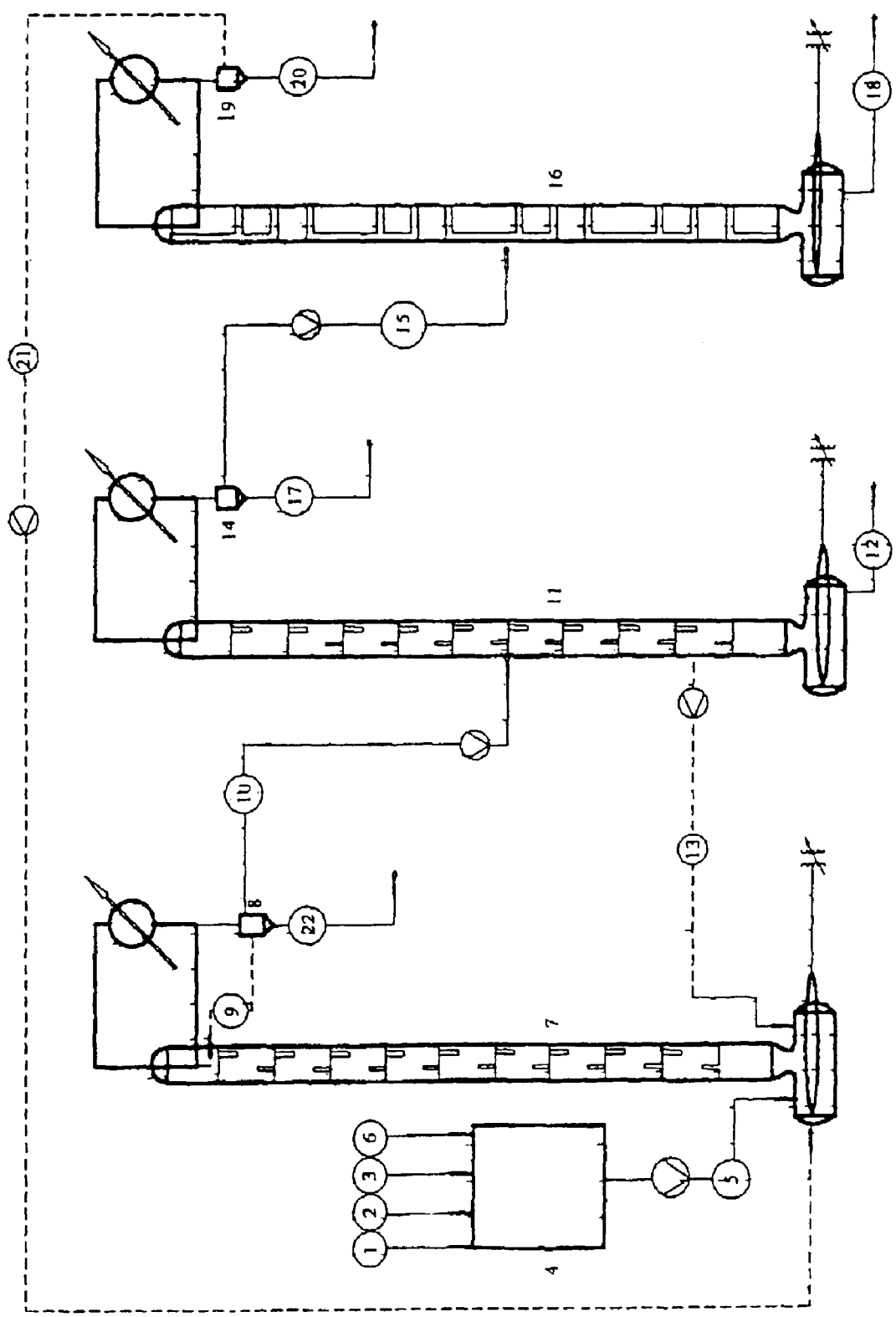
FIG. 1 is a flow diagram of a preferred embodiment of the instant invention.

Surprisingly, the desired low-boiling or higher-boiling ester compound which azeotropic mixtures forming in the presence of the water to be eliminated, so that the monocarboxylic acid has the highest boiling point among the three starting compounds.

Such a choice of the starting compounds ensures that the carboxylic acid is completely retained in the esterification reactor.

The mixture of two alcohols which is used for the coupled production of two carboxylic esters can vary over wide ranges in its composition. In general, the composition of the alcohol mixture is in the range of 90:10% by weight to 10:90% by weight, preferably in the range of 80:20% by weight to 20:80% by weight and in particular of 70:30% by weight to 30:70% by weight, of the respective alcohols, based on the total mass of the alcohol mixture to be used. Alcohol mixtures in which the azeotropic mixtures advantageously complement one another with respect to their water requirement are preferably employed.

In the case of the coupled production of ethyl acetate and butyl acetate, particularly advantageous azeotropic mixtures can be established with the use of an alcohol mixture having an ethanol content of 70% by weight and a butanol content of 30% by weight, based on the total mass of the alcohol mixture to be used. In the case of the coupled production of ethyl acetate and isopropyl acetate, it is advisable to use a starting mixture having an ethanol content of 80% by weight and an isopropanol content of 20% by weight, based on the total mass of the alcohol mixture to be used, in order to utilize a particularly advantageous formation of the azeotropic mixture.

The total amount of alcohols which is fed into the esterification reactor corresponds in general to the number of equivalents of the respective carboxylic acid which are fed in, since unconverted alcohol is generally stripped from the water of reaction and recycled to the reaction. When the esterification reaction is carried out continuously, it is therefore sufficient to use the amount of alcohols corresponding to the number of equivalents of carboxylic acid present. The alcohol also acts as an azeotrope former and thus serves as an entraining agent for removing the water of reaction.

Further process variants comprise removing the water of reaction with passage of an inert gas or with application of reduced pressure.

The esterification of carboxylic acids with alcohols is a process known from the prior art. The esterification can be carried out in the absence of a catalyst, with the advantage that the addition of a foreign substance is avoided. In this case, the carboxylic acid simultaneously acts as a reactant for the alcohol and as a catalyst. However, it is then generally necessary to maintain higher reaction temperatures in order to enable the reaction to take place at a sufficiently high rate. Furthermore, an excessive thermal load may lead to damage to the ester and a deepening of the color.

In general, however, conventional esterification catalysts, such as, for example, sulfuric acid, phosphoric acid, p-toluenesulfonic acid or methanesulfonic acid, are used. In order to avoid or to inhibit corrosion phenomena, methanesulfonic acid or p-toluenesulfonic acid is preferably used. The concentration of the esterification catalyst is in general from 0.5 to 3% by weight, based on the total reaction mixture.

The esterification reaction is carried out in general at atmospheric pressure or at pressures of 0.001 to 0.3 MPa and at temperatures in the range of 60 to 180° C. The reaction conditions to be established in each case depend on the starting materials used and on the chosen process variant, on whether, for example, the reaction is carried out in the presence of a catalyst or whether reduced pressure is applied for removing the water of reaction.

Preferably, the esterification reaction is carried out continuously in an esterification column in which the bottom of the column also referred to as a distillation boiler, serves as a reaction vessel and the attached column tower serves as a distillation column for rectifying and removing the ester compounds already formed, the unreacted alcohol and the water of reaction, the rectification following the esterification reaction simultaneously completely retaining the carboxylic acid in the distillation boiler. The column pressure, the column temperature and the reflux ratio to be set at the top of the column depend on the starting compounds to be used in each case. Usually, atmospheric pressure is employed. Column temperature, top temperature and reflux ratio are set so that no carboxylic acid passes via the top of the column into the ester distilled off but at the same time sufficient water of reaction is discharged.

The mixture leaving the top of the column is condensed and passes into the phase separator after the fraction recycled as reflux into the esterification column has been separated off, water of reaction and organic phase separating from one another. Depending on the choice of the starting compounds, the reflux can be supplemented by adding organic or aqueous phase for the formation of an azeotropic mixture. The resulting organic crude ester mixture is then purified by distillation by the process according to the invention.

The crude ester mixture obtained in a vessel after a batchwise process variant or preferably in an esterification column after a continuous process variant is then added to the first distillation column, preferably to the middle region of the column, particularly preferably between the 15th and 25th tray, calculated from the bottom of the column. A material stream which has a higher concentration of the alcohol component having the higher boiling point is taken off below the feed point of the crude ester, preferably in the stripping section and particularly preferably between the 2nd and 10th tray, calculated from the bottom of the column, and is recycled to the esterification reactor. Pure higher-boiling ester compound, for example butyl acetate, is taken off via the bottom of the first distillation column, while the volatile components, predominantly comprising the lower-boiling ester compound, contaminated with small amounts of the low-boiling alcohol and residual amounts of water, are removed via the top of the first distillation column. Column temperature, column pressure and reflux ratio in the first distillation column depend on the ester mixture to be separated in each case.

The low-boiling crude ester, e.g. crude ethyl acetate, leaving the top of the first distillation column is condensed and is fed to a phase separator after the amount required for the reflux into the first distillation column has been separated off, residual amounts of water being separated off. The organic crude product is then purified in a second distillation column to remove further residual amounts of water and the amounts of the low-boiling alcohol. The feed to the second distillation column is preferably to the middle region of the second distillation column, particularly to the 10th to 20th tray, calculated from the bottom of the column. The pure low-boiling ester compound, e.g. pure ethyl acetate, is taken off via the bottom, while the top product is first fed to a phase separator after condensation and removal of the amount required for the reflux into the second distillation column. The organic phase is recycled to the esterification reactor. The aqueous phase saturated with alcohol compounds and ester compounds is combined with the aqueous phases obtained after phase separation of the condensed top products from the esterification column and from the first distillation column and is freed from the organic components in a downstream water stripping column. The starting alcohols recovered thereby are recycled to the esterification reactor.

The coupled production of two ester compounds is a particularly economical process since capital costs can be reduced by omitting columns in the esterification part and in the working-up part. The reduced operation of distillation columns likewise reduces the steam consumption, which leads to an additional energy saving. Furthermore, two distillation processes can be controlled by only a single control. Finally, the use of the azeotropic mixtures leads to a more efficient elimination of water, so that less water has to be circulated or evaporated.

Surprisingly, the two ester compounds can be obtained in excellent purity from the distillation columns via the bottom take-offs and can be used without further purification steps for most applications. The removal of the pure products via the bottom is particularly advantageous because the main product need not be completely vaporized again and the reflux ratio and the amount of steam used in the distillation columns can be varied over wide ranges without the quality of the ester compounds taken off via the bottom being impaired.

Even if the composition of the alcohol mixture varies within wide limits, which may range from 90:10% by weight to 10:90% by weight of the respective alcohols, based on the total mass of the alcohol mixture to be used, the desired ester compounds can be obtained in excellent purity by the process according to the invention.

An exemplary embodiment of the invention is described in more detail below with reference to the process flow diagram shown in the figure. The invention is not intended to be restricted in any way thereby.

The known part of the process has already been described further above, and therefore only the reference numerals are mentioned here: 1 aliphatic carboxylic acid, 2 and 3 respective aliphatic alcohols, 4 premixer, material stream 5, starting mixture fed to the bottom of the esterification column 7, 6 catalyst, 7 esterification column containing catalysts in the bottom, 8 phase separator, 9 supplementation of azeotropic mixture, material stream 10 comprising organic crude mixture taken off from the phase separator 8, material stream 22 comprising aqueous phase taken off from the phase separator 8.

According to the invention, the material stream 10 is fed to the middle region of the first distillation column 11. The pure ester compound which has the higher boiling point of the two ester compounds prepared by the coupled production is taken off via the bottom of the distillation column 11 and via the material stream 12. Below the feed point of the crude ester, the material stream 13 containing an amount of the higher-boiling alcohol is taken off via a side take-off in the stripping section of the distillation column 11 and is recycled into the bottom of the esterification column 7. The top take-off is fed to the phase separator 14 after condensation and removal of the amount required for the reflux into the distillation column 11 and is separated into an organic phase and an aqueous phase. The organic phase, material stream 15, is fed to the middle region of the second distillation column 16, while the aqueous phase, material stream 17, is discharged. The pure low-boiling ester compound is obtained via the bottom take-off, material stream 18 of the second distillation column, while the volatile components are fed to the phase separator 19 after condensation and removal of the amount required for the reflux ratio. The residual water, material stream 20, is discharged via the phase separator 19, while the organic phase separated off is recycled as material stream 21 to the bottom of the esterification column 7.

The water streams 22, 17 and 20 obtained at the phase separators 8, 14 and 19 can be combined and then freed from the residual contents of alcohols and ester compounds in a known manner by means of a water stripping column. The alcohols recovered are recycled to the esterification process.

The following example is intended to describe the process according to the invention, but without restricting it.

Coupled production of ethyl acetate and butyl acetate

In the premixer 4, ethanol 1, butanol 2 and acetic acid 3 are mixed so that a mixture having the following percentage composition is obtained:

| | |
|---|---|
| Ethanol | 24.6% by weight |
| Butanol | 24.6% by weight |
| Acetic acid | 50.8% by weight | and said mixture is introduced as a material stream 5 into the bottom of the esterification column. The bottom of the esterification column contains 2.0% by weight, based on the total reaction mixture, of methanesulfonic acid as catalyst 6. The esterification column 7, equipped with 45 trays, is operated at atmospheric pressure and a top temperature of 83° C. The top product is condensed, cooled and is passed through the phase separator 8 with removal of the amount recycled as reflux into the esterification column 7. Product 9 is recycled from the organic phase to the top of the esterification column in an amount such that a reflux ratio of 2:3 is established, while the remainder is fed, as material stream 10, having the following composition

| | |
|---|---|
| Ethanol | 1.0% by weight |
| Butanol | 0.6% by weight |
| Acetic acid | 0.0% by weight |
| Ethyl acetate | 53.0% by weight |
| Butyl acetate | 43.1% by weight |
| Water | 2.3% by weight, | to the 20th tray (counted from the bottom of the column) of the first distillation column 11. The distillation column 11 is operated at atmospheric pressure and at a top temperature of 74° C. From the top take-off of the distillation column 11, the product, after condensation, is recycled to the top in an amount such that a reflux ratio of 1:2 is ensured. The remaining amount of product obtained at the top of the distillation column 11 is separated in the phase separator 14 into the organic phase 15 and the aqueous phase 17. The material stream 15 removed from the phase separator 14 has the following composition

| | |
|---|---|
| Ethanol | 1.8% by weight |
| Butanol | 0.0% by weight |
| Acetic acid | 0.0% by weight |
| Ethyl acetate | 94.1% by weight |
| Butyl acetate | 0.0% by weight |
| Water | 4.1% by weight. |

From the 5th tray, counted from the bottom of the column, of the distillation column 11, a side stream 13 having the following composition

| | |
|---|---|
| Ethanol | 0.0% by weight |
| Butanol | 2.8% by weight |
| Acetic acid | 0.0% by weight |
| Ethyl acetate | 0.8% by weight |
| Butyl acetate | 96.3% by weight |
| Water | 0.1% by weight | is removed and is recycled to the bottom of the esterification column 7.

Pure butyl acetate (material stream 12) having the following composition

| | |
|---|---|
| Ethanol | 0.0% by weight |
| Butanol | 0.2% by weight |
| Acetic acid | 0.0% by weight |
| Ethyl acetate | 0.0% by weight |
| Butyl acetate | 99.8% by weight |
| Water | <0.1% by weight | is obtained via the bottom of the distillation column 11.

The material stream 15 is fed to the middle region (17th tray, counted from the bottom of the column) of the distillation column 16, which is operated at atmospheric pressure and at a top temperature of 69° C. Pure ethyl acetate (material stream 18) having the following composition

| | |
|---|---|
| Ethanol | 0.1% by weight |
| Butanol | 0.0% by weight |
| Acetic acid | 0.0% by weight |
| Ethyl acetate | 99.9% by weight |

-continued

| | |
|---|---|
| Butyl acetate | 0.0% by weight |
| Water | <0.1% by weight | is obtained via the bottom of the column 16.

After condensation, product is recycled from the top take-off of the distillation column 16 to the top in an amount such that a reflux ratio of 3:1 is established. The remaining amount of top product is passed to the phase separator 19. The organic phase separated off is recycled as material stream 21 having the following composition

| | |
|---|---|
| Ethanol | 3.3% by weight |
| Butanol | 0.0% by weight |
| Acetic acid | 0.0% by weight |
| Ethyl acetate | 91.8% by weight |
| Butyl acetate | 0.0% by weight |
| Water | 4.9% by weight | into the bottom of the esterification column 7.

The aqueous streams 22, 17 and 20 obtained at the phase separators 8, 14 and 19 have the following composition
Material stream 22

| | |
|---|---|
| Ethanol | 2.7% by weight |
| Butanol | 0.2% by weight |
| Acetic acid | 0.0% by weight |
| Ethyl acetate | 3.4% by weight |
| Butyl acetate | 0.3% by weight |
| Water | 93.4% by weight |

Material streams 17, 20

| | |
|---|---|
| Ethanol | 7.3% by weight |
| Butanol | 0.0% by weight |
| Acetic acid | 0.0% by weight |
| Ethyl acetate | 7.8% by weight |
| Butyl acetate | 0.0% by weight |
| Water | 84.9% by weight |

As shown by the examples according to the invention, in the coupled production of two ester compounds, the desired ester compounds 12 and 18 can be obtained via the bottom of the two distillation columns 11 and 16 in a purity such that they can be used in most applications without further purification steps.

The invention claimed is:

1. A process for the coupled production of ethyl acetate and butyl acetate or ethyl acetate and i-propyl acetate by reacting a mixture of ethanol and butanol or of ethanol and i-propanol with acetic acid and working up the crude ester mixture by distillation, wherein after the water of reaction has been separated off, the crude ester mixture leaving the esterification reactor is fed to a first distillation column, in which a side stream containing the higher-boiling alcohol component is taken off below the feed point of the crude ester and is recycled to the esterification reactor, in which the essentially pure butyl acetate or i-propyl acetate is taken off via bottom of the first distillation column and in which, after water has been separated off, a top take-off is fed to a second distillation column, in which the essentially pure ethyl acetate is taken off via the bottom of the second distillation column and in which, after water has been separated off, the top take-off is recycled to the esterification reactor.

2. The process as claimed in claim 1, wherein the side stream is removed from the first distillation column, below the feed point of the crude ester, in a stripping section at $2^{nd}$ to $10^{th}$ tray, and is recycled to the esterification reactor.

3. The process as claimed in claim 1 wherein the crude ester mixture is fed to a middle region of the first distillation column.

4. The process as claimed in claim 1 wherein a top takeoff from the first distillation is fed to a middle region of the second distillation column.

5. The process as claimed in claim 1 wherein the amount of the respective alcohol component is in the range from 10–90% by weight based on the alcohol mixture.

6. The process as claimed in claim 1 wherein the esterification reaction is carried out in the presence of an esterification catalyst having a concentration of from 0.5 to 3% by weight, based on the total reaction mixture.

7. The process as claimed in claim 1 wherein the esterification reactor is an esterification column having a column bottom and attached column tower.

8. The process of claim 3 wherein the middle region is comprised of the $15^{th}$ to $25^{th}$ trays of the first distillation column.

9. The process of claim 4 wherein the middle region is the $10^{th}$ to $20^{th}$ trays of the second distillation column.

10. The process of claim 5 wherein the amount of alcohol component is 20 to 80% by weight, based on the alcohol mixture.

11. The process of claim 5 wherein the amount of alcohol component is 30 to 70% by weight, based on the alcohol mixture.

* * * * *